(12) United States Patent
Yip et al.

(10) Patent No.: US 7,413,574 B2
(45) Date of Patent: Aug. 19, 2008

(54) DRUG-ELUTING STENT COVER METHOD OF USE

(75) Inventors: Philip S. Yip, San Jose, CA (US); James Jacobs, Mountain View, CA (US); Syed Hossainy, Fremont, CA (US); Jon Becker, Danville, CA (US); Timothy A. Limon, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 77 days.

(21) Appl. No.: 11/497,652

(22) Filed: Aug. 1, 2006

(65) Prior Publication Data
US 2006/0271165 A1    Nov. 30, 2006

Related U.S. Application Data

(62) Division of application No. 10/334,034, filed on Dec. 30, 2002, now Pat. No. 7,105,018.

(51) Int. Cl.
*A61F 2/06* (2006.01)
(52) U.S. Cl. .................. 623/1.15; 623/903
(58) Field of Classification Search ....... 623/1.11–1.48, 623/903
See application file for complete search history.

(56) References Cited

U.S. PATENT DOCUMENTS

| | | | |
|---|---|---|---|
| 3,839,743 A | 10/1974 | Schwarcz | |
| 4,346,028 A | 8/1982 | Griffith | |
| 4,377,337 A | 3/1983 | Beck et al. | |
| 4,417,576 A | 11/1983 | Baran | |
| 4,423,725 A | 1/1984 | Baran et al. | |
| 4,633,873 A | 1/1987 | Dumican et al. | |
| 4,656,083 A | 4/1987 | Hoffman et al. | |
| 4,718,907 A | 1/1988 | Karwoski et al. | |

(Continued)

FOREIGN PATENT DOCUMENTS

DE     36 40 745     6/1987

(Continued)

OTHER PUBLICATIONS

Bull, "Parylene Coating for Medical Applications", Medical Product Manufacturing News, 2 pgs, Mar. 1993.

(Continued)

*Primary Examiner*—Suzette J Gherbi
(74) *Attorney, Agent, or Firm*—Squire, Sanders & Dempsey, L.L.P.

(57) ABSTRACT

An intravascular stent includes an eluting sheath fabricated from a mesh for controlled release of therapeutic drugs and for delivery of the therapeutic drugs in localized drug therapy in a blood vessel. The eluting sheath is attached to at least a portion of an outside surface area of the stent structure and is fabricated from a mesh designed to neck down in response to a radially outward directed force resulting in the uniform expansion of the stent. The eluting sheath can be loaded with at least one therapeutic drug for the release thereof at a treatment site to facilitate repair of a damaged vessel. The stent has a high degree of flexibility in the longitudinal direction, yet has adequate vessel wall coverage and radial strength sufficient to hold open an artery or other body lumen.

24 Claims, 5 Drawing Sheets

U.S. PATENT DOCUMENTS

| | | |
|---|---|---|
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,816,339 A | 3/1989 | Tu et al. |
| 4,877,030 A | 10/1989 | Beck et al. |
| 4,878,906 A | 11/1989 | Lindemann et al. |
| 4,879,135 A | 11/1989 | Greco et al. |
| 4,902,289 A | 2/1990 | Yannas |
| 4,994,298 A | 2/1991 | Yasuda |
| 5,019,090 A | 5/1991 | Pinchuk |
| 5,059,211 A | 10/1991 | Stack et al. |
| 5,062,829 A | 11/1991 | Pryor et al. |
| 5,064,435 A | 11/1991 | Porter |
| 5,084,065 A | 1/1992 | Weldon et al. |
| 5,085,629 A | 2/1992 | Goldberg et al. |
| 5,100,429 A | 3/1992 | Sinofsky et al. |
| 5,108,370 A | 4/1992 | Walinsky |
| 5,108,755 A | 4/1992 | Daniels et al. |
| 5,123,917 A | 6/1992 | Lee |
| 5,151,105 A | 9/1992 | Kwan-Gett |
| 5,156,623 A | 10/1992 | Hakamatsuka et al. |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,192,311 A | 3/1993 | King et al. |
| 5,197,977 A | 3/1993 | Hoffman, Jr. et al. |
| 5,199,951 A | 4/1993 | Spears |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,330,500 A | 7/1994 | Song |
| 5,342,348 A | 8/1994 | Kaplan |
| 5,342,621 A | 8/1994 | Eury |
| 5,356,433 A | 10/1994 | Rowland et al. |
| 5,383,928 A | 1/1995 | Scott et al. |
| 5,389,106 A | 2/1995 | Tower |
| 5,411,551 A | 5/1995 | Winston et al. |
| 5,413,597 A | 5/1995 | Krajicek |
| 5,419,760 A | 5/1995 | Narcisco, Jr. |
| 5,421,955 A | 6/1995 | Lau et al. |
| 5,439,446 A | 8/1995 | Barry |
| 5,441,515 A | 8/1995 | Khosravi et al. |
| 5,458,605 A | 10/1995 | Klemm |
| 5,514,154 A | 5/1996 | Lau et al. |
| 5,527,337 A | 6/1996 | Stack et al. |
| 5,578,075 A | 11/1996 | Dayton |
| 5,605,696 A | 2/1997 | Eury et al. |
| 5,700,286 A | 12/1997 | Tartaglia et al. |
| 5,707,385 A | 1/1998 | Williams |
| 5,780,807 A | 7/1998 | Saunders |
| 5,830,217 A | 11/1998 | Ryan |
| 5,843,172 A | 12/1998 | Yan |
| 6,004,348 A | 12/1999 | Banas et al. |
| 6,131,266 A | 10/2000 | Saunders |
| 6,146,322 A | 11/2000 | Papirov et al. |
| 6,152,869 A | 11/2000 | Park et al. |
| 6,168,602 B1 | 1/2001 | Ryan |
| 6,254,632 B1 | 7/2001 | Wu et al. |
| 6,261,316 B1 | 7/2001 | Shaolian et al. |
| 6,261,320 B1 | 7/2001 | Tam et al. |
| 6,273,908 B1 | 8/2001 | Ndondo-Lay |
| 6,379,381 B1 | 4/2002 | Hossainy et al. |
| 6,391,033 B2 | 5/2002 | Ryan |
| 6,419,692 B1 | 7/2002 | Yang et al. |
| 6,436,132 B1 | 8/2002 | Patel et al. |
| 6,491,720 B1 * | 12/2002 | Vallana et al. ............. 623/1.42 |
| 6,530,950 B1 | 3/2003 | Alvarado et al. |
| 6,540,776 B2 | 4/2003 | Sanders Millare et al. |
| 6,613,084 B2 * | 9/2003 | Yang ........................ 623/1.42 |
| 6,629,992 B2 | 10/2003 | Bigus et al. |
| 6,629,994 B2 | 10/2003 | Gomez et al. |
| 6,663,665 B2 | 12/2003 | Shaolian et al. |
| 6,899,727 B2 | 5/2005 | Armstrong et al. |
| 6,939,368 B2 | 9/2005 | Simso |
| 7,163,553 B2 * | 1/2007 | Limon ....................... 623/1.15 |
| 2002/0138129 A1 | 9/2002 | Armstrong et al. |
| 2003/0078647 A1 | 4/2003 | Vallana et al. |
| 2003/0114919 A1 | 6/2003 | McQuiston et al. |
| 2003/0166779 A1 | 9/2003 | Khemani et al. |
| 2003/0181973 A1 | 9/2003 | Sahota |
| 2003/0212447 A1 | 11/2003 | Euteneuer et al. |

FOREIGN PATENT DOCUMENTS

| | | |
|---|---|---|
| DE | 44 07 079 | 9/1994 |
| EP | 0 567 788 | 11/1993 |
| EP | 0 604 022 | 1/1994 |
| EP | 0 578 998 | 6/1994 |
| EP | 0 621 017 | 10/1994 |
| EP | 0 623 354 | 11/1994 |
| WO | WO 91/17789 | 11/1991 |
| WO | WO 93/06792 | 4/1993 |
| WO | WO 95/29647 | 11/1995 |

OTHER PUBLICATIONS

Casper et al., "Fiber-Reinforced Absorbable Composite for Orthopedic Surgery", Science and Engineering, vol. 53, pp. 497-501, Fall Meeting 1985.

Hahn et al., "Glow Discharge Polymers as Coatings for Implanted Devices", Univ. of Missouri, pp. 109-113, 1981.

Hahn et al., "Biocompability of Glow-Discharge-Polymerized Films and Vacuum-Deposited Parylene", Applied Polymer Symposium 38, pp. 55-64, 1984.

Kelley et al., "Totally Resorbable High-Strength Composite Material", Advances in Biomedical Polymers, Ed. By Charles G. Gebelein, pp. 75-85, 1987.

Muller et al., "Advances in Coronary Angioplasty: Endovascular Stents", Coronary Artery Disease, vol. 1, No. 4, 10 pgs, 1990.

Nichols et al., "Electrical Insulation of Implantable Devices by Composite Polymer Coatings", Univ. of Missouri, Paper No. 87-0110, pp. 57-62, 1987.

Olson "Parylene, a Biostable Coating for Medical Applications", Nova Tran Parylene Coating Services Jul. 25, 1988 and Nov. 14, 1988, 10 pgs.

"Parylene Conformal Coating" by Nova Tran Custom Coating Services, 8 pgs, undated.

Schatz "A View of Vascular Stents", Arizona Heart Institute Foundation, Phoenix Arizona, 15 pgs, 1988.

Schmidt et al., "Long-Term Implants of Parylene-C Coated Microelectrodes", Medical & Biological Engineering & Computing, pp. 96-101, 1988.

Shing-Chiu Wong et al., "An Update on Coronary Stents", Cardio, Feb. 1992, 8 pgs.

* cited by examiner

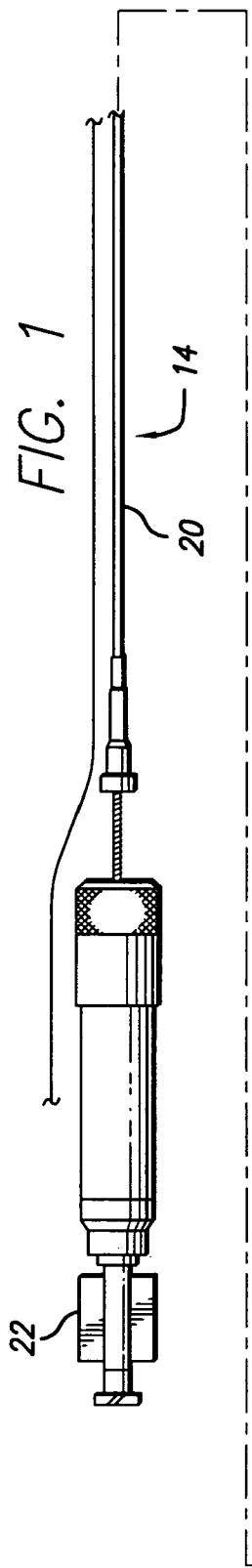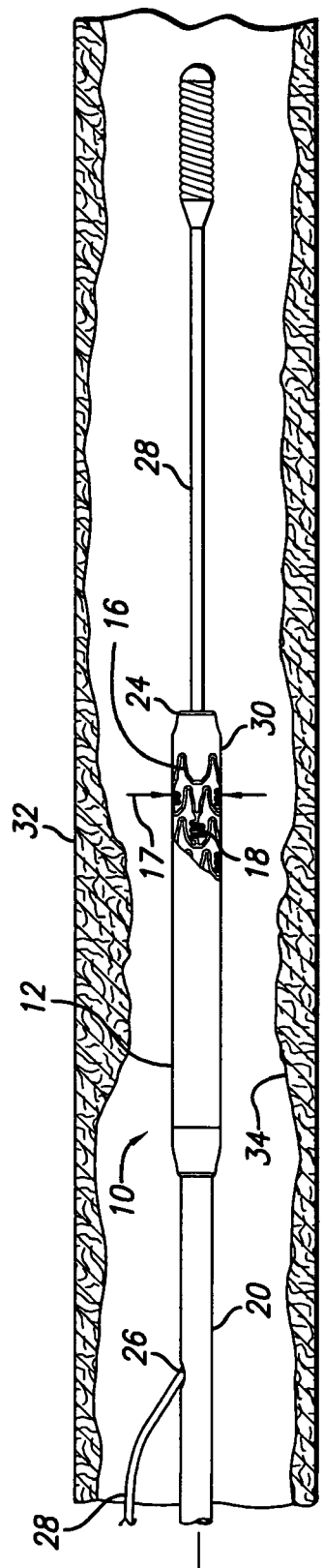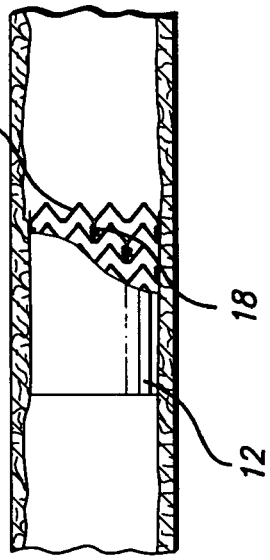

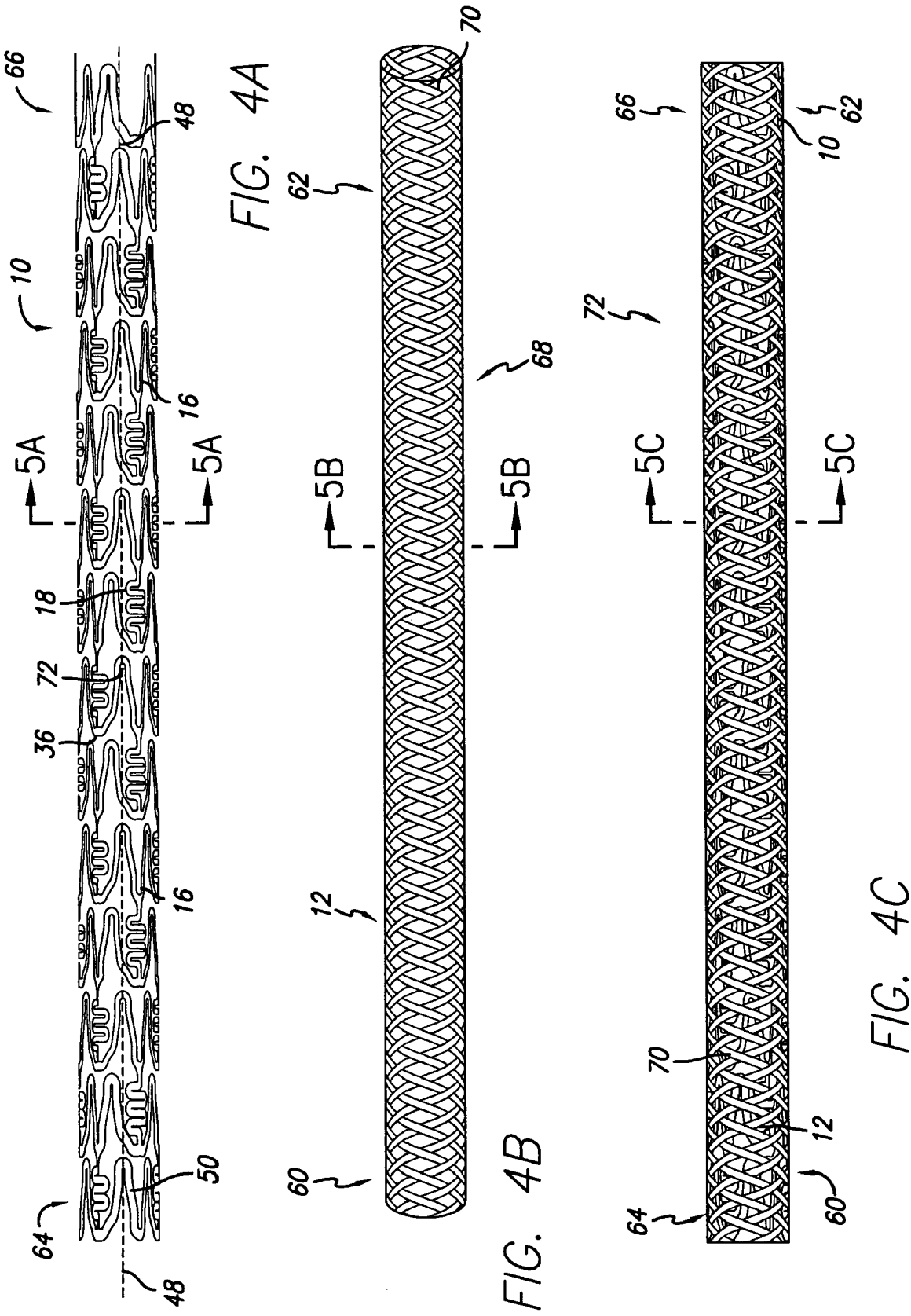

DRUG-ELUTING STENT COVER METHOD OF USE

CROSS REFERENCE TO RELATED APPLICATION

This is a divisional application of U.S. patent application Ser. No. 10/334,034, which was filed on Dec. 30, 2002 now U.S. Pat. No. 7,105,108.

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels. More particularly, the invention concerns an intravascular device having a prefabricated, patterned mesh stent cover that helps to prevent the formation and release of embolic debris in the body lumen and is capable of eluting therapeutic drugs with uniform and controlled drug distribution at the treatment site while providing the intravascular device with a uniform patterned biocompatible and/or hemocompatible surface.

An intravascular interventional device such as a stent is particularly useful in the treatment and repair of blood vessels after a stenosis has been treated by percutaneous transluminal coronary angioplasty (PTCA), percutaneous transluminal angioplasty (PTA), or removed by atherectomy or other means, to help improve the results of the procedure and reduce the possibility of restenosis. Stents also can be used to provide primary compression to a stenosis in cases in which no initial PTCA or PTA procedure is performed. While stents are most often used in the procedures mentioned above, they also can be implanted in any body lumen or vessel such as the urethra, esophagus and bile duct and the like.

In typical PTCA procedures, a guiding catheter or sheath is percutaneously introduced into the cardiovascular system of a patient through the femoral arteries and advanced through the vasculature until the distal end of the guiding catheter is in the aorta. A guide wire and a dilatation catheter having a balloon on the distal end are introduced through the guiding catheter with the guide wire sliding within the dilatation catheter. The guide wire is first advanced out of the guiding catheter into the patient's vasculature and is directed across the arterial lesion. The dilatation catheter is subsequently advanced over the previously advanced guide wire until the dilatation balloon is properly positioned across the arterial lesion. Once in position across the lesion, the expandable balloon is inflated to a predetermined size with a radiopaque liquid at relatively high pressure to press the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty. In angioplasty procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. Stents are generally cylindrically shaped devices which function to hold open and sometimes expand a segment of a blood vessel or other arterial lumen, such as coronary artery. Stents are usually delivered in a compressed condition to the target location and then are deployed into an expanded condition to support the vessel and help maintain it in an open position. The stent is usually crimped tightly onto a delivery catheter and transported in its delivery diameter through the patient's vasculature. The stent is expandable upon application of a controlled force, often through the inflation of the balloon portion of the delivery catheter, which expands the compressed stent to a larger diameter to be left in place within the artery at the target location. The stent also may be of the self-expanding type formed from, for example, shape memory metals or superelastic nickeltitanum (NiTi) alloys, which will automatically expand from a compressed state when the stent is advanced out of the distal end of the delivery catheter into the body lumen.

Since it is often useful to provide localized therapeutic pharmacological treatment of a blood vessel at the location being treated with the stent, it is also desirable to provide stents with a biocompatible and/or hemocompatible surface coating of a polymeric material with the capability of being loaded with therapeutic agents, to function together with the intravascular devices for placement and release of the therapeutic drugs at a specific intravascular site. Drugs can also be loaded on a stent without using a polymer coat, for example, by chemical linkage. Drug-eluting stent devices have shown great promise in treating coronary artery disease, specifically in terms of reopening and restoring blood flow in arteries stenosed by atherosclerosis. Restenosis rates after using drug-eluting stents during percutaneous intervention are significantly lower compared to bare metal stenting and balloon angioplasty.

The above-described, non-surgical interventional procedures, when successful, avoid the necessity for major surgical operations. However, a danger which is always present during these procedures is the potential for particles of the atherosclerotic plaque, which can be extremely friable, breaking away from the arterial wall. For example, during deployment of a stent, the metal struts of the stent can possibly cut into the stenosis and shear off pieces of plaque which become embolic debris that will travel downstream and lodge somewhere in the patient's vascular system. When any of the above-described procedures are performed in the carotid arteries, the release of emboli into the circulatory system should be avoided. For example, debris that is carried by the bloodstream to distal vessels of the brain can cause these cerebral vessels to occlude, possibly resulting in a stroke. Therefore, although cerebral percutaneous transluminal angioplasty has been performed in the past, the number of procedures performed has been limited due to the fear of causing an embolic stroke should embolic debris enter the bloodstream and block vital downstream blood passages. Embolization in other vasculature may induce possible acute myocardial infraction when a procedure is performed on the coronary arteries and gangrene when performed in peripheral arteries, such as the arms and legs. In addition, current design and fabrication methods for drug-eluting stent devices are not optimal. Accordingly, various limitations exist with respect to such current design and fabrication methods for drug-eluting stents.

While stents are helpful in holding open otherwise blocked or occluded vessels, the stent does have an open structure which may include struts and spines which cooperatively provide the scaffolding necessary to maintain the vessel open at the site of treatment. Due to the open nature of the stent structure, there is a possibility that growth material can pass through the openings between the struts and extend into the inner lumen of the stent structure. For example, excessive cell or tissue growth (intimal hyperplasia) can cause partial restenosis to develop over time, which is detrimental to the patient. The tissue or cell growth can extend into the tubular opening created by the stent and can block or otherwise reocclude the opening and can possibly cause abnormal blood flow through the stent which can cause formation of thrombi that are detrimental to the patient's health.

Prior art devices have been created to help reduce the passage of such growth through the wall of the deployed stent, including a stent covering which surrounds the open stent. In this manner, the gaps between the stent struts can be covered to prevent material, such as plaque, from prolapsing between the struts. Coverings have included a variety of materials such as ePTFE, autologous vein grafts, pericardium and fibrin. The covering should be sufficiently flexible and expandable to allow the stent to deploy from its collapsed or compressed position to a fully expanded position.

Covered stents also help prevent the struts from cutting into the plaque of the stenosis which helps reduce the possibility of forming embolic debris that can be released into the blood stream, as described above. Moreover, in the event that any embolic debris may be created from the expansion of the stent, the covering could trap the embolic particles against the arterial wall, thus preventing the particles from being released into the bloodstream.

Some prior art covered stents are difficult to manufacture due to the flexibility of the covering and the requirement that the covering be capable of expansion when the stent is deployed within the patient's vasculature. For these reasons, the material used to form the covering may be subjected to intricate processing to obtain the desired flexibility for the covering and to attach the covering to the stent. A covering which does not expand normally can cause the stent to misalign within the body vessel and can cause an non-uniform deployment of the stent. Moreover, some coverings are made from a sheet of material which is rolled into a cylindrical shape by creating a longitudinal seam which runs along the length of the covering and then the covering is attached to the stent. Such coverings can be more susceptible to tearing, especially at the seam, when the stent is expanded.

Some prior art stents that are covered may have a tendency to shorten when expanded and the covered material also shortens, providing an undesirable result. As the stent and the covered material are expanded into contact with an artery or vessel wall, the shortening movement may scrape along the artery wall and cause injury or dislodge plaque material which may embolize. Further, as these prior art covered stents shorten upon expansion, the cover material shortens past the stent struts at the stent ends, leaving a covered stent with exposed stent struts, and not fully covered upon expansion.

Moreover, the addition of drug elution to the stent adds a whole new set of engineering challenges. Current design and fabrication methods for drug-eluting stent devices are not optimal. One limitation, for example, is that current drug eluting stent designs employ spray techniques in which a mixture of the drug in a polymer and/or solvent solution is spray coated on the entire stent surface with a primer, drug, and topcoat layers being used to control release kinetics. This approach tends to cause cracking in the drug-coating layer, since the layer also undergoes stretching during stent expansion, and a considerable amount of the drug is washed out into the blood stream, and only a fraction gets into the tissue/artery. Further, the amount of the drug that can be loaded on the stent is limited by mechanical properties of the coating, since a higher drug content in the polymer makes the coating more brittle and causes cracking thereto. Therefore, loading a higher drug dose requires coating with more polymer on the device. Moreover, the spray techniques require large spaces to avoid webbing and pooling. Special equipment for crimping the drug-eluting stent on the balloon and to securely attach the stent on the balloon is also needed in accordance with current fabrication methods. Often spray coatings may be damaged during the crimping processes. Stents designed for acute deliverability may not make the optimal elution vehicles.

What has been needed and heretofore unavailable is a novel design that decouples the two major functional characteristics of the drug-eluting stent device, namely the purely mechanical stent structure and the local drug-eluting component. Current devices are constrained by their design construct which necessitates optimizing both factors-mechanical stent expansion and drug-elution kinetics simultaneously. Thus, it would be desirable to have a stent structure that is optimally designed for expansion (i.e., allowable stress/strain, scaffolding, radial strength, etc.) independent of the drug-eluting component, and the drug-eluting component designed for local drug release independent of mechanical factors associated with stent expansion. The present invention meets these and other needs.

SUMMARY OF THE INVENTION

Briefly, and in general terms the present invention is directed to intraluminal devices, and more particularly, to a drug-eluting stent delivery system for controlled release of therapeutic drugs and for delivery of the therapeutic drugs in localized drug therapy in a blood vessel. In one aspect, the drug-eluting stent delivery system includes a separate elution sheath that is applied over the stent and loaded with at least one therapeutic drug for the controlled release of therapeutic drugs at a treatment site. Methods for making different types of a drug-eluting stent delivery system are also disclosed herein.

In one embodiment, the present invention provides for a drug-eluting stent delivery system for controlled release of therapeutic drugs and for delivery of the therapeutic drugs in localized drug therapy in a blood vessel. A pattern of struts are interconnected to form a structure that contacts the walls of a body lumen to maintain the patency of the vessel. The pattern of struts can include a plurality of flexible cylindrical rings being expandable in a radial direction with each of the rings having a first delivery diameter and a second implanted diameter while aligned on a common longitudinal axis. At least one link of the stent is attached between adjacent rings to form the stent. The stent is formed at least in part of a metallic material such as stainless steel, platinum, titanium, tantalum, nickel-titanium, cobalt-chromium or alloys thereof. Stents of other strut patterns are also possible.

A stent cover defining an eluting sheath fabricated from a mesh is placed over the stent and is loaded with at least one therapeutic drug for the release thereof at a treatment site. The eluting sheath is attached to at least a portion of an outside surface area of the stent structure at selected locations including at the stent distal end and proximal end such that the covering is free to stretch in the midsection to a form conforming to the environment as the device expands without shortening to allow for uniform stretching during expansion. Various therapeutic drugs that can be used in combination with the polymeric sleeve include antiplatelets, anticoagulants, antifibrins, antithrombins, anti-inflammatories and antiproliferatives. Several drug-loadable polymers, such as poly(methyl(meth)acrylate ("PMMA"), ethylenevinylalcohol ("EVAL"), poly(butyl(meth)acrylate) ("PBMA"), biodegradable polymers (i.e., poly(glycolic acid) ("PGA"), poly (L-lactic acid) ("PLLA"), polyethylene glycol ("PEG"), polyester amide ("PEA"), hyaluronic acid ("HA"), poly (glycerol-sebacate) ("PGS") (developed by Yadong Wang, MIT), and thermoplastic rubber can be used to fabricate the mesh eluting sheath of the invention. The thickness of the drug-loaded polymeric sleeve ranges from about 0.005 to about 0.1 mm (0.0002 to 0.004 inches).

In one aspect, the eluting sheath of the drug delivery system is fabricated from a random mesh pattern or a predesigned stent pattern having drugloaded elements to form a desired local drug-elution profile. The random mesh and the predesigned stent pattern of the eluting sheath can be formed in situ by weaving, solution spinning, etching or cutting. The mesh eluting sheath can be prefabricated in a desired dimension by using one of the known polymer processing techniques in the art including extrusion, injection molding, laser cutting, and slip casting. As a further mechanism of controlling elution of the therapeutic drug at the treatment site, the eluting sheath can be coated with at least one additional layer of polymer material and/or hydrophilic material as a barrier layer.

In use, the drug-loaded mesh stent cover is designed to plastically deform, neck down or break in response to a radially directed force resulting from the expansion of the stent and the drug-loaded elements are held against the blood vessel wall by the stent structure. The drug loaded mesh stent cover also is designed to tear and deform on demand as a side branch is accessed by a second catheter. In certain applications, the mesh stent cover is fabricated to expand along a length of the stent to overcome strain.

In another embodiment, the present invention provides for a drug-eluting stent delivery system for controlled release of therapeutic drugs and for delivery of the therapeutic drugs in localized drug therapy in a blood vessel. The thickness of the mesh stent cover varies to conform to the variable thickness of the stent to yield a uniform radial thickness. This mesh stent cover can be coupled with any variable thickness stent.

In another embodiment, the present invention provides for a drug-eluting stent delivery system for controlled release of therapeutic drugs and for delivery of the therapeutic drugs in localized drug therapy in a blood vessel. A pattern of struts are interconnected to form a first stent structure that contacts the walls of a body lumen to maintain the patency of the vessel, wherein a second stent structure, fabricated as a prepatterned thin metallic or porous ceramic sheet having a polymer layer disposed thereon, is loaded with at least one therapeutic drug for the release thereof at a treatment site. The second stent structure is attached to at least a portion of an outside surface area of the first stent structure. The second stent structure can be wrapped around the first stent structure in a sleeve-like configuration.

In another embodiment, the eluting sheath is fabricated as a prepatterned woven fabric with a fabric design that is stretchable in two dimensions. The eluting sheath is then attached to the outside surface area of the first stent structure by being wrapped around the first stent structure in a sleeve-like configuration and is attached to the stent by an adhesive.

In a further embodiment, the present invention provides for a drug-eluting stent delivery system for controlled release of therapeutic drugs and for delivery of the therapeutic drugs in localized drug therapy in a blood vessel. A pattern of struts are interconnected to form a first stent structure that contacts the walls of the body lumen to maintain the patency of the vessel. In a second stent structure, the stent cover defining an eluting sheath is fabricated from a mesh with a web-like pattern and is placed over the stent and attached to at least a portion of the outside surface area of the stent. The mesh stent cover is configured to cooperate with the stent to accomplish controlled and uniform expansion of the stent.

The stent cover configured of a mesh with a web-like pattern defining an eluting sheath is placed over the stent and is loaded with at least one therapeutic drug for the release thereof at a treatment site. The eluting sheath is attached to at least a portion of an outside surface area of the stent structure at selected locations including at the stent distal end and proximal end such that the covering is free to stretch in the mid-section to a form that conforms to the environment as the device expands without shortening to allow uniform stretching during expansion.

In another embodiment, the mesh stent cover with the web-like pattern can have weakened points at selected locations to allow for non-random breakage during expansion such that all the web mesh members remain attached to the mesh and are not free to float away from the overall structure of the device and allow for side branch access. Alternatively, the web pattern could include undulations in both the longitudinal and circumferential direction such that the mesh is flexible and is easily expandable. Yet in another embodiment, the mesh cover can be designed to have a pattern similar to a variety of stent patterns including the following coronary stent systems from Advanced Cardiovascular Systems, Inc., Santa Clara, Calif.: the Multi-Link Penta™, the Multi-Link TETRA D™, the Multi-Link Vision™, the Multi-Link FRONTIER™; in addition, to other stent systems such as BX Velocity™ Stent (Cordis Corporation located in Miami Lakes, Fla.), and the Express Stent (Boston Scientific Inc. located in Natick, Mass.).

The mesh stent cover having a web-like pattern is fabricated from a polymeric material selected from the group consisting of acetal copolymer, acetal homopolymer, acrylonitrile butadiene styrene, ABS and polycarbonate, nylon, polyamide, polyacrylate, polyaryl sulfone, polycarbonate, polyetherketone, polyetherimide, polyether sulfone, polyethylene terephthalate, polyimide, polyphenylene oxide, polyphenylene sulfide, polypropylene, polysulfone, polyurethane, polyvinyl chloride, styrene acrylonitrile. The thickness of the drug-loaded polymeric sleeve ranges from about 0.005 to about 0.1 mm (0.0002 to 0.004 inches). Alternatively, the stent cover configured of a mesh with a web-like pattern defining an eluting sheath can be fabricated from biocompatible metals and alloys.

In yet another embodiment, the present invention provides for a method of making a drug-eluting stent delivery system for controlled release of therapeutic drugs and for delivery of the therapeutic drugs in localized drug therapy in a blood vessel. The method includes providing a pattern of struts interconnected to form a structure that contacts the walls of a body lumen to maintain the patency of the vessel and attaching a stent cover defining an eluting sheath fabricated from a mesh to at least a portion of an outside surface area of the stent structure. The eluting sheath is loaded with at least one therapeutic drug for the release thereof at a treatment site. Various therapeutic drugs that can be used in combination with the eluting sheath include antiplatelets, anticoagulants, antifibrins, antithrombins, anti-inflammatories and antiproliferatives. The stent assembly is then placed intraluminally at the repair site within the vasculature. In response to a radially directed force provided by a stent, balloon catheter or a self expanding stent, the mesh stent cover necks down or breaks to accomplish controlled expansion of the stent assembly.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within an artery.

FIG. 3A is an elevational view, partially in section, depicting the expanded stent within the artery after withdrawal of the delivery catheter.

FIG. 4A is a side view of a cylindrical stent of the invention which illustrates the pattern of the stent shown in FIGS. 1-3 in an unexpanded condition.

FIG. 4B is a perspective view of a eluting component defined by a mesh stent cover of the drug-eluting stent delivery system in accordance with the invention shown in the unexpanded condition.

FIG. 4C is a side view of the drug-eluting stent delivery system in accordance with the invention shown in the unexpanded condition.

DETAILED DESCRIPTION OF THE PREFERRED EMBODIMENTS

Figure 3B:
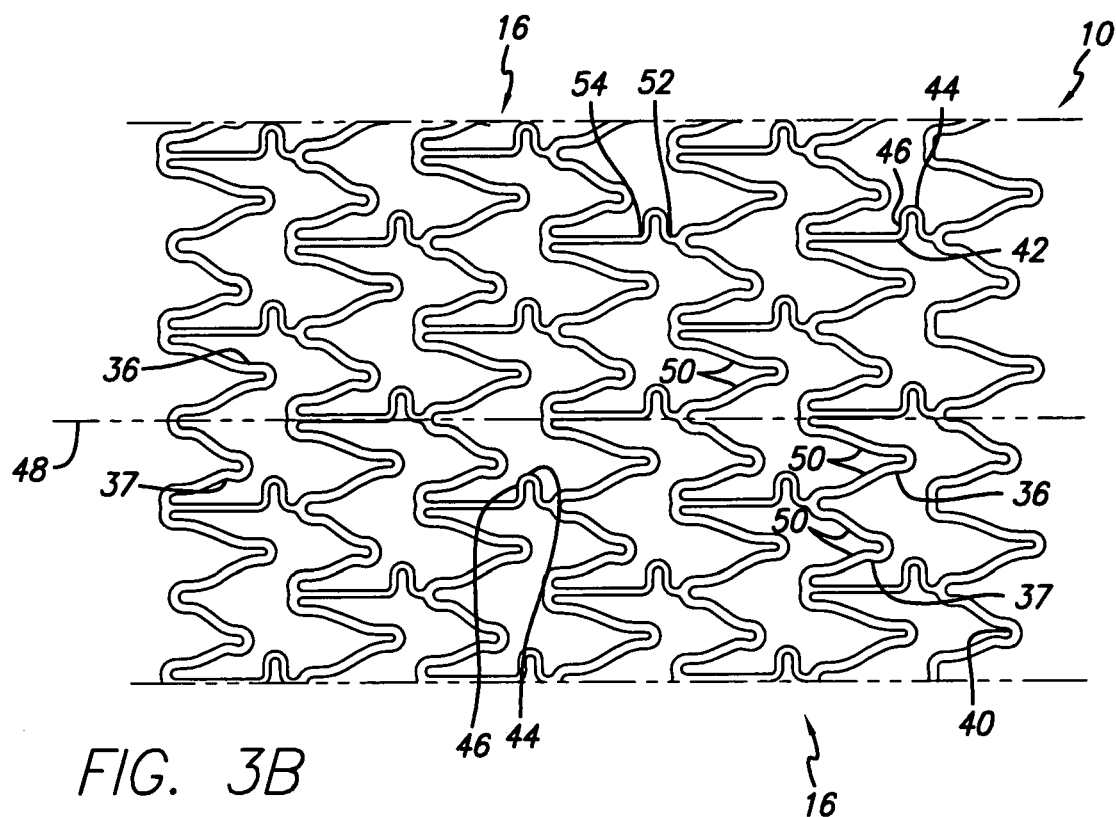
FIG. 3B is a top view of a flattened stent of another embodiment of the invention which illustrates the pattern of the rings and links.

As shown in the drawings for purposes of illustration, the present invention is directed to a drug-eluting stent delivery system which includes a mechanical component, the intravascular stent, and a drug-eluting component, a stent cover defining an eluting sheath fabricated from a mesh placed over the stent for controlled release of therapeutic drugs and for delivery of the therapeutic drugs in a localized drug therapy in a blood vessel. Also disclosed are methods of making a drug-eluting stent delivery system having a drug-eluting component disposed in the form of a prepatterned mesh with a web-like pattern for controlled release and delivery of therapeutic drugs in localized drug therapy in a blood vessel.

Turning to the drawings, FIG. 1 depicts an embodiment of a metallic stent 10, coupled with an eluting sheath defined by a mesh stent cover 12, incorporating features of the invention, mounted on a catheter assembly 14 which is used to deliver the stent and implant it in a body lumen, such as a coronary artery, carotid artery, peripheral artery, or other vessel or lumen within the body. The stent generally comprises a plurality of radially expandable cylindrical rings 16 disposed generally coaxially and interconnected by undulating links 18 disposed between adjacent cylindrical rings. The catheter assembly includes a catheter shaft 20 which has a proximal end 22 and a distal end 24. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 14 as depicted in FIG. 1 is of the well known rapid exchange type which includes an RX port 26 where the guide wire 28 will exit the catheter. The distal end of the guide wire 28 exits the catheter distal end 24 so that the catheter advances along the guide wire on a section of the catheter between the RX port 26 and the catheter distal end 24. As is known in the art, the guide wire lumen which receives the guide wire is sized for receiving various diameter guide wires to suit a particular application. The stent is mounted on the expandable member 30 (balloon) and is crimped tightly thereon so that the stent and expandable member present a low profile diameter for delivery through the arteries.

As shown in FIG. 1, a partial cross-section of an artery 32 is shown with a small amount of plaque that has been previously treated by an angioplasty or other repair procedure. Stent 10 of the present invention is used to repair a diseased or damaged arterial wall which may include the plaque 34 as shown in FIG. 1, or a dissection, or a flap which are commonly found in the coronary arteries, carotid arteries, peripheral arteries and other vessels.

In a typical procedure to implant stent 10, the guide wire 28 is advanced through the patient's vascular system by well known methods so that the distal end of the guide wire is advanced past the plaque or diseased area 34. Prior to implanting the stent, the cardiologist may wish to perform an angioplasty procedure or other procedure (i.e., atherectomy) in order to open the vessel and remodel the diseased area. Thereafter, the stent delivery catheter assembly 14 is advanced over the guide wire so that the stent is positioned in the target area. The expandable member or balloon 30 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3A, the balloon is fully inflated with the stent expanded and pressed against the vessel wall, and in FIG. 3A, the implanted stent remains in the vessel after the balloon has been deflated and the catheter assembly and guide wire have been withdrawn from the patient.

The stent 10 serves to hold open the artery 32 after the catheter is withdrawn, as illustrated by FIG. 3A. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3A.

FIG. 3B is another embodiment of stent 10, the stent is formed so that each cylindrical ring includes a first peak 36 and a second peak 38 and valleys 40. Although the stent is not divided into separate elements, for ease of discussion references to peaks and valleys is appropriate. The number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery. The height of the second peaks of the cylindrical rings of the stent are shorter than the height of the first peaks. In addition, the cylindrical rings also include at least one undulating link 42, which has at least one curved portion 44 connected to a substantially straight portion 46. The substantially straight portion may be perpendicular to the stent longitudinal axis 48.

Figure 3C:
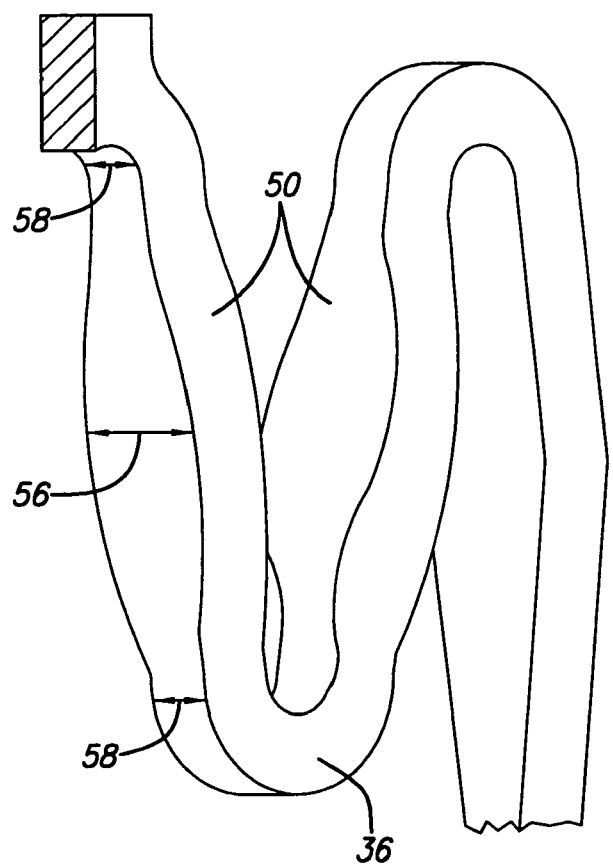
FIG. 3C is an enlarged partial perspective view of a portion of a peak and associated struts depicting variable thickness struts.

FIG. 3C illustrates another aspect of stent 10, the stent is formed so that the various struts 50 of the cylindrical rings 16 (FIG. 3B) and the undulating links 42, all can be formed so that each has a variable radial thickness along the stent length. For example the undulating links and its associated arms 52, 54 may be thicker at one end (arm 52) than at the other end of the link (arm 54). Further, struts 50 (FIG. 3C) may vary in radial thickness along their length in order to create variable flexibility in the cylindrical rings 16. As shown in FIG. 3C first peak 36 has struts 50 that have radial thick portion 56 in the middle of the struts and radial thin portion 58 near the ends of the struts. In another example, the rings at for example the proximal end of the stent may be thicker radially than the rings in the center of the stent.

The stent patterns shown in FIGS. 1-3C are for illustration purposes only and can vary in size and shape to accommodate different vessels or body lumens. Further, the metallic stent 10 is of a type that can be used in accordance with the present invention.

The drug-eluting component 12 (i.e., stent cover defining an eluting sheath fabricated from a mesh) of the drug-eluting stent delivery system of the present invention is applicable to all vascular stent applications in the body including coronary and peripheral arterial system. It is further contemplated that the mesh eluting sheath is thinner than the stent structure such that the stent provides the structural support to maintain the patency of the vessel. The mesh cover does not provide significant structural support. Further, the present invention can be used in the treatment of vulnerable plaque such as thin fibrous-capped atheromatic vulnerable lesions using desired drug and release kinetics with site specificity. In addition, the drug-eluting component of the stent system can be incorporated on all stent platforms for all sizes and lengths including the following stent systems from Advanced Cardiovascular Systems: the Multi-Link Penta™, the Multi-Link TETRA™, the Multi-Link Vision™, the Multi-Link FRONTIER™; in addition, to other stent systems such as BX Velocity™ Stent (Cordis Corporation located in Miami Lakes, Fla.), and the Express Stent (Boston Scientific Inc. located in Natick, Mass.) to achieve uniform drug distribution along the entire vessel including the carmna. It is also contemplated that the drug-eluting component of the present invention can be used for designing drug-eluting stent devices with thinner stent struts (i.e., thickness ranging between 0.4 mm-1.1 mm (0.02-0.05 inches)) without compromising the structural integrity of the stent, deliverability and optimal drug elution.

The present invention overcomes all of the earlier mentioned limitations through a novel design that decouples the two major functional characteristics of the drug-eluting stent delivery system, namely the purely mechanical stent structure and the local drug-eluting component. The stent structure is optimally designed for expansion (i.e., allowable stress/strain, scaffolding, and radial strength). In the present invention, each component is independently designed and optimized for its functional characteristics and the optimal drugeluting stent delivery system is conceived and assembled.

As shown in one embodiment, in FIG. 4A a stent of the drug-eluting stent delivery system illustrates the pattern of the stent shown in FIGS. 1-3A in an unexpanded condition. The stent 10 is shown in a tubular or cylindrical configuration so that the pattern can be clearly viewed. The stent is typically formed from a tubular member, however, it can be formed from a flat sheet rolled into a cylindrical configuration.

FIG. 4B shows a polymeric mesh cover defining an eluting sheath 12 of the stent 10 in accordance with the invention shown in a tubular configuration. In this embodiment, the stent which has a mesh cover that is flexible and deforms plastically upon expansion for release of therapeutic drugs and for delivery of the therapeutic drugs in localized drug therapy in a blood vessel, includes a pattern of struts 50 (FIG. 4A) interconnected to form a structure that contacts the walls of a body lumen to maintain the patency of the vessel. The pattern of struts include flexible cylindrical rings 16 (FIG. 4A) being expandable in a radial direction, each of the rings having a first delivery diameter and a second implanted diameter and being aligned on a common longitudinal axis 48. At least one link 18 (FIG. 4A) of the stent is attached between adjacent rings to form the stent. The link can have curves for enhancing flexibility or it can be straight (not shown), depending upon the particular application.

With further reference to FIG. 4B, the drug-eluting polymeric mesh cover 12 is prefabricated in the desired dimensions using conventional polymer processing methods known in the art, including extrusion, injection molding, slip casting, braiding or plasma polymerization using a mixture of the polymer, solvent and drug in liquid, semi-solid or solid form. The polymeric mesh cover can be fabricated either as a random mesh 68 or as a prepatterned solid tube (not shown). The random mesh pattern of the stent cover can be prepared by methods known in the art such as in situ by weaving or solution spinning. The mesh may be deposited on the stent by the relative movement of a nozzle and the stent such that there is no set pattern and the resulting mesh cover structure is inherently random. Alternatively, the mesh can be braided on the stent, after a 3-D CAD design. In yet another embodiment, the mesh is co-braided or co-meshed with metal for reinforcement when coupled with a stent designed to have thin struts and less metal (not shown). Each spun mesh member or subset of mesh members is then loaded with different amounts or type of therapeutic drug. Alternatively, a second metal mesh is used between the polymeric mesh of the expanding stent structure. When the polymeric mesh is fabricated as a solid tube, the predesigned pattern can be attained by the known methods in the art consisting of laser cutting or etching using the excimer or the avia solid-state laser without any post processing. The prepatterned polymeric mesh cover is fabricated from a predesigned stent pattern loaded with a therapeutic drug to form a desired local drug-elution profile. The intent of the predesigned pattern of the eluting sheath is to enable the deformation of the drug-eluting mesh cover upon stent expansion (FIG. 6A). Accordingly, in one embodiment, upon stent expansion, the drug-loaded polymeric mesh cover plastically deforms and necks down in response to a radially directed force and the individual drug-loaded mesh members 70 are held against the vessel wall by the expanded stent structure.

In another embodiment, the mesh cover is fabricated from a predesigned stent pattern such that selected locations of the mesh cover break at random locations of the selected locations during expansion and individual drugloaded mesh-web members are held against the vessel wall by the expanded stent structure. The predesigned stent pattern can be fabricated so that it expands along a length of the stent if needed to overcome strain during expansion. It is contemplated that in certain embodiments, since the mesh is not made from a solid tube, the blood can access the cell wall and allow for epithilization. It is further contemplated that the mesh has more than 5% open area (i.e., an area on the cylinder without material to contact the tissue) before expansion which can range from about 30% to about 99% or about 50% to about 85% open area. Depending on the desired nature of local drug elution and drug uptake into the artery, a variety of different patterns can be etched or cut into the polymeric mesh that forms the cover.

The mesh cover 12 may also include a radiopaque element selected from a group consisting of gold and platinum, which serves as a marker and allows the physician to avoid overlap when a second stent is inserted into a body lumen. In addition, the mesh cover can also include a least one therapeutically active radioactive isotope, which serves to inhibit cell growth.

The mesh cover 12 can be attached to selected locations on the stent 10 to allow for uniform stent expansion. In one embodiment, the mesh cover has a proximal end 60 and a distal end 62 which are attached to the proximal end 64 and distal end 66 of the stent 10 using conventional metal-polymer or polymer-polymer adhesion techniques such as adhesive bonding, shrink bonding, laser bonding, and the like. In order to secure the mesh cover to the stent, only a small portion of the mesh cover material needs to be bonded to the stent. In another embodiment not all the struts are attached, as the device expands portions of the mesh may slide on some of the struts to distribute the stress more evenly on the mesh. It is also contemplated that in yet another embodiment, the mesh cover material is not interconnected such that the individual mesh members 70 are not attached to each other, but are held in place by the stent structure 10. Further, the drug-loaded polymeric mesh has a thickness in the range of about 0.005 to about 0.1 mm (0.0002 to 0.004 inches). An adhesive such as medical grade silicone can be used to bond the mesh cover material 12 to the stent. It is also contemplated that the adhesive can be biologically active. The adhesive could be thinned using organic solvent such as ethyl acetate. The covered stent could then be placed in an oven to remove the excess solvent and to cure the bond. By way of example, suitable bonds have been achieved by placing covered stents in an oven for about 15 minutes at 150° Celsius. It should be appreciated, however, that the duration in the oven, along with the oven temperature, can be varied to achieve suitable cure. The bonding agent which can be utilized to bond the ends of the mesh covering to that of the present invention can be a curable adhesive or organic solvent. A primer can be used to facilitate the chemical bond between the mesh covering and the stent. It should be appreciated that heat can be applied to the bonding agents, via an oven or other thermal source, to help in the curing and increase bond strength.

In FIG. 4C the drug-eluting stent delivery system 72, which includes a stent 10 with the drug-eluting component or polymeric mesh 12 disposed thereon in accordance with the invention is shown in the unexpanded condition.

Figure 5A:
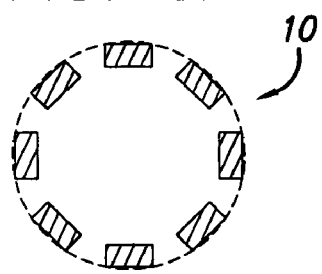
FIG. 5A is a transverse, cross-sectional view taken along lines 5A-5A depicting the drug-eluting stent delivery system in FIG. 4A shown in the unexpanded condition.
Figure 5B:
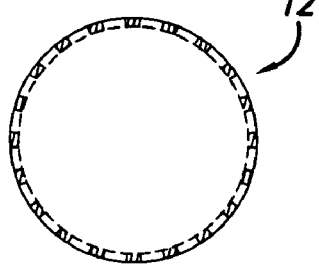
FIG. 5B is a transverse, cross-sectional view taken along lines 5B-5B depicting the drug-eluting component of the drug-eluting stent delivery system in FIG. 4B shown in the unexpanded condition.
Figure 5C:
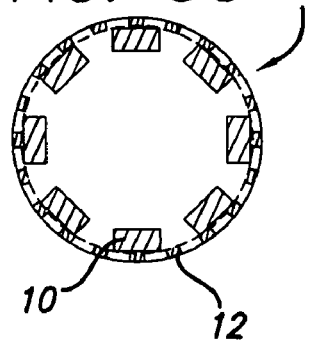
FIG. 5C is a transverse, cross-sectional view taken along line 5C-5C depicting the drug-eluting stent delivery system in FIG. 4C shown in the unexpanded condition.

FIGS. 5A-C depict various views of the two separate components of the drug-eluting stent delivery system, namely the mechanical stent structure 10 and the drug-eluting sheath or mesh cover 12, and one embodiment of the present invention drug-eluting stent delivery system 72 in an unexpanded condition. More specifically, FIG. 5A shows the stent in FIG. 4A in the unexpanded condition; FIG. 5B shows the drug-eluting component of the stent in FIG. 4B in the unexpanded condition; and FIG. 5C shows the stent with the drug-eluting sheath disposed thereon in the unexpanded condition.

Figure 6:
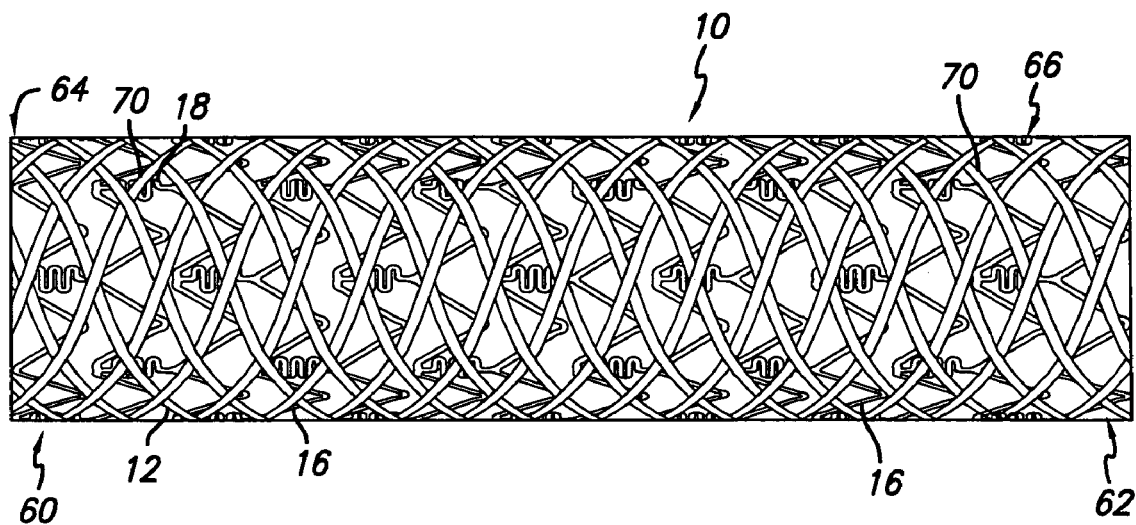
FIG. 6 is a partial side view of the drug-eluting stent delivery system in accordance with the invention shown in the expanded condition.

FIG. 6 illustrates a plan view of the stent 10 with the drug-eluting component fabricated from a polymeric mesh 12 disposed thereon in accordance with the invention shown in the expanded condition. The present invention further contemplates that the drug-loaded polymeric mesh cover can have at least one additional layer of polymer material and/or hydrophilic coating as a barrier layer to control elution of the therapeutic drug at the treatment site (not shown). Multiple layers of polymer material disposed on the polymeric mesh cover provide further control of the elution of the therapeutic drug at the treatment site. When the stent expands from that shown in FIG. 4 to that shown in FIG. 6, by the action of the stent, self-expanding stent, or the inflated balloon, the individual mesh members 70 deform plastically and neck down such that the individual members slide relative to one another as the stent expands. Thus, the mesh cover material does not interfere with the radial expansion of the stent and does not contribute to stent foreshortening, if any.

Figure 7:
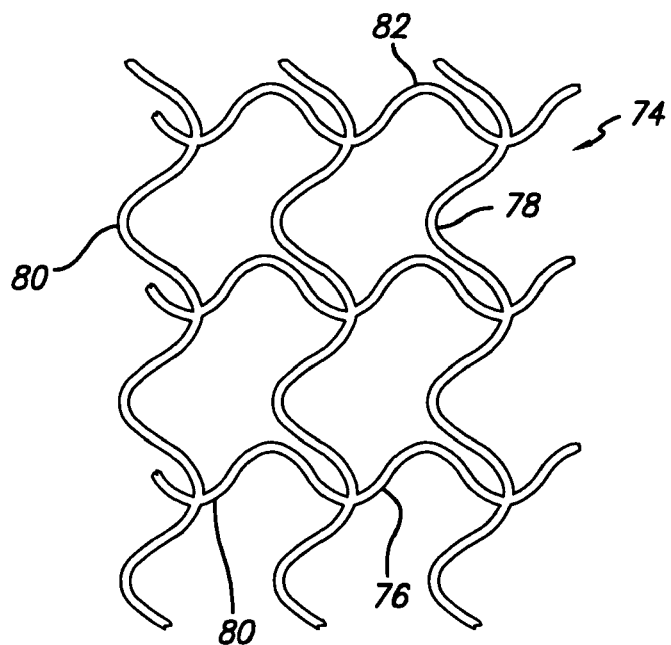
FIG. 7 is an enlarged partial view of an alternative embodiment depicting the drug-eluting sheath defined by a web-like pattern.

As shown in FIG. 7, an alternative embodiment of the mesh cover 12 is configured in a web-like pattern 74 and has two dimensional undulations in both the circumferential 76 as well as the longitudinal 78 direction. The width and radial thickness of the individual struts 80 of the web pattern can be varied to provide flexibility. When the cross-section of one stent strut 80 is less than the cross-section of another stent strut, the strut with the smaller cross-section generally will have greater flexibility. The undulations 76 and 78 provide flexibility and allow the mesh cover to neck down or break in response to a radially outward directed force provided by the stent, the balloon catheter, by a self-expanding stent, or an intermediate water swellable sleeve. Thus, the mesh cover with the web pattern facilitates stent expansion and does not contribute to stent foreshortening, if any. In yet another embodiment (not shown), the mesh cover can be designed to have a pattern similar to any of the stent patterns described previously. In one embodiment, the mesh includes cylindrical rings and undulating links which form a series of openings that are smaller than the openings formed by the cylindrical rings and undulating links of stent from which the mesh is patterned. Furthermore, the cylindrical rings and undulating links of the mesh may have smaller dimensions (i.e., the width or thickness) than the stent counterpart.

Figure 8:
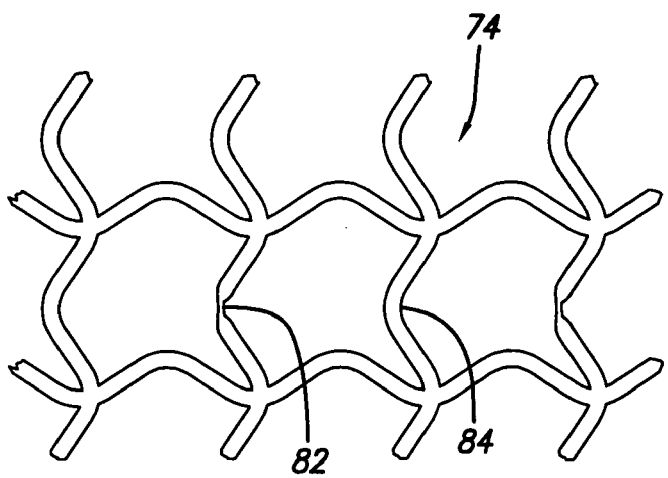
FIG. 8 is an enlarged partial view of an alternative embodiment of the invention depicting a mesh stent cover with a web-like pattern.

FIG. 8 shows an alternative embodiment in which the mesh cover with a web-like pattern 74 has weakened points 82 at selected locations to allow for non-random breakage during expansion in response to a radially directed force provided by a stent, balloon catheter or self expanding stent. The weakened points 82 can be made by a reduced cross-section of the individual mesh members with a web-like pattern. By way of example, when the stent covering is expanded beyond a predetermined point by the action of the stent, self expanding stent, inflated balloon or the an intermediate water swellable sleeve, the weakened points on the individual web members 84 will break and allow for side branch access or radial expansion of the stent. Thus, stent radial expansion is not hindered and stent foreshortening will not result.

Figure 9:
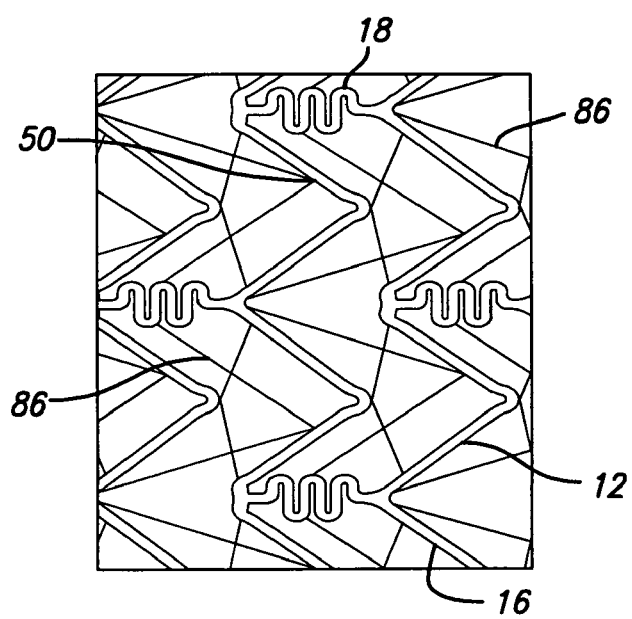
FIG. 9 is an enlarged partial view of an alternative embodiment depicting a mesh cover with a web like pattern.

FIG. 9 depicts another embodiment in which the drug-eluting sheath 12 can be defined by a random mesh 86 spanning the struts 50 of stent 10. The random mesh structure is achieved by the deposition of the mesh on the stent by the relative movement of a nozzle and the stent. For example the nozzle may disperse the molten or solvent liquidified mesh material while the nozzle moves along the longitudinal axis of the stent as the stent rotates thereby forming an inherently random shape. Other patterns such as s-shape, spiral, helical, corkscrew, or any other patterns known in the art can also be created. The random mesh structure is configured to allow the individual mesh members 70 to plastically deform and slide relative to one another as the stent expands. It can also be contemplated that this pattern can also include undulations 76 and 78 and weakened points 82 to aid in uniform expansion as the stent expands. For example, the weakened points 82 can break when the stent is expanded from about 150 percent to about 400 percent form a first delivery diameter. In another embodiment where the individual mesh members do not include weakened points the mesh cover will remain intact and withstand stent expansion beyond 400 percent such that the individual mesh members do not break in response to the stent expansion. In one embodiment the stent begins with a compressed diameter of about 1.0 mm (0.04 inches) and can be made to expand to a larger diameter of 3.0 mm (0.12 inches) resulting in a circumferential expansion of about 196 percent. In yet another embodiment the stent expansion from a compressed state may yield a larger diameter of 4.5 mm (0.18 inches) resulting in a circumferential expansion of about 345 percent. It is contemplated that the mesh cover can neck down or break to accommodate the resultant circumferential expansion Thus, the mesh cover material does not interfere with the expansion of the stent and does not contribute to stent foreshortening.

In another alternative embodiment (not shown), a pattern of struts 50 are interconnected to form a first stent structure that contacts the walls of a body lumen to maintain the patency of the vessel. A second stent structure, fabricated as a prepatterned thin metallic sheet having a polymer layer disposed thereon, is loaded with at least one therapeutic drug for the release thereof at a treatment site, the second stent structure being attached to at least a portion of an outside surface area of the first stent structure. It should be appreciated that the second stent structure is not limited to a tubular form, and can be fabricated as a thin metallic sheet attached to the outside surface area of the first stent structure by being wrapped around the first stent structure in a sleeve-like configuration. In the second stent structure, the eluting component can also be fabricated as a prepatterned porous ceramic having a polymer layer disposed thereon, and loaded with at least one therapeutic drug for release thereof at the treatment site. Various mechanisms for attaching the second stent structure to the outside surface area of the first stent structure are known in the art and are used with the present invention. Examples of attachment mechanisms include metal-polymer and polymer-polymer bonding technologies, such as adhesives and other similar methods.

In yet another embodiment (not shown), the present invention provides for a drug-eluting stent delivery system for controlled release of therapeutic drugs and for delivery of the therapeutic drugs in localized drug therapy in a blood vessel. A pattern of struts are interconnected to form a first stent structure that contacts the walls of a body lumen to maintain the patency of the vessel. A second stent structure, fabricated as a prepatterned tubular woven fabric with a fabric design that is stretchable in two dimensions can be used to make a tubular stent covering. Generally, polymeric fibers are more flexible than metallic fibers and are more suitable for making woven fabric coverings. Using elastomeric materials for such two way stretchable design can provide additional stretchability in expansion. The mesh cover with the web pattern can be woven to provide openings large enough to allow blood access to the tissue through the openings.

Examples of various metals or alloys used in forming the mechanical stent structure of the present invention drug-eluting stent delivery system include stainless steel, platinum, titanium, tantalum, nickel-titanium, cobalt-chromium, and alloys thereof. The stent can also be formed of a polymeric material such as poly(methyl(meth)acrylate ("PMMA"), Poly(glycolic acid) ("PGA") or poly(L-lactic acid) ("PLLA").

Examples of various polymers used in forming the drug-eluting component, the mesh cover 12 of the drug-eluting stent delivery system for all of the embodiments, include poly(methyl(meth)acrylate ("PMMA"), ethylenevinylalcohol ("EVAL"), poly(butyl(meth)acrylate) ("PBMA"), biodegradable polymers (i.e., Poly(glycolic acid) ("PGA") and poly(L-lactic acid) ("PLLA"), polyethylene glycol ("PEG"), hyaluronic acid ("HA"), polyester amide ("PEA"), poly (glycerol-sebacate) ("PGS") (developed by Yadong Wang, MIT), nanoscale structures of carbon, acetal copolymer, acetal homopolymer, acrylonitrile butadiene styrene, ABS and polycarbonate, nylon, polyamide, polyacrylate, polyaryl sulfone, polycarbonate, polyetherketone, polyetherimide, polyether sulfone, polyethylene terephthalate, polyimide, polyphenylene oxide, polyphenylene sulfide, polypropylene, polysulfone, polyurethane, polyvinyl chloride, styrene acrylonitrile and other suitable polymers. It is contemplated that the above polymers can be slowly dissolved or chemically degraded or both. As set forth above, the local drug-eluting component may be alternatively fabricated from porous ceramic or various metals or alloys, including stainless steel, platinum, titanium, tantalum, nickel-titanium, cobalt-chromium, and alloys thereof.

The eluting sheath is also loaded with therapeutic drugs which will be released in the area of treatment to improve the device's performance within the body vessel by significantly lowering the restenosis rates. For example, in one embodiment the mesh is braided on the stent and each spun mesh member or subset of mesh members can be loaded with different amount and type of therapeutic drug. Examples of therapeutic drugs or pharmacologic compounds that may be loaded into the prefabricated random or patterned mesh stent cover 12 and delivered to the target site in the vasculature include a therapeutic drug selected from the group consisting essentially of taxol, aspirin, prostaglandins, and the like. Various therapeutic agents such as antithrombogenic or antiproliferative drugs are used to further control local thrombosis. Examples of therapeutic agents or drugs that are suitable for use in accordance with the present invention include sirolimus, everolimus, actinomycin D (ActD), taxol, paclitaxel, or derivatives and analogs thereof. Examples of agents include other antiproliferative substances as well as antineoplastic, anti-inflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, anti-inflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-argchloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinbiastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from HoffmanLaRoche located in Basel, Switzerland), or Lisinopril® (available from Merck located in Whitehouse Station, N.J.); calcium channel blockers (such as Nifedipine), coichicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents are known in the art. The calculation of dosages, dosage rates and appropriate duration of treatment are previously known in the art. Furthermore, the therapeutic drugs or agents are loaded at desired concentration levels per methods well known in the art to render the device ready for implantation.

The present invention also provides for various methods of making a drug-eluting stent delivery system for controlled release of therapeutic drugs and for delivery of the therapeutic drugs in localized drug therapy in a blood vessel. In one embodiment, the method includes providing a pattern of struts interconnected to form a structure that contacts the walls of a body lumen to maintain the patency of the vessel. A mesh cover, fabricated from a random mesh or as a prepatterned tube, is attached to at least a portion of an outside surface area of the stent structure. The mesh cover is fabricated by using a variety of different techniques known in the art which include extrusion, laser cutting, plasma polymerization, slip casting, injection molding, braiding and similar techniques. The pattern of the polymeric tube may assume any desirable pattern which works to achieve an appropriate local drug-elution profile.

The drug-loaded, prepatterned polymeric sleeve is preferably attached to the stent structure in the final stages of fabricating the drug-eluting stent delivery system, after the stent is crimped and securely attached to the balloon using current technology. The polymeric sleeves or filament strands of appropriate length are attached to the outer surface of the stent on the delivery system using various metal-polymer and polymer-polymer bonding technologies, such as adhesives. The mesh cover 12 can be attached to selected locations on the stent to allow for uniform expansion. In one embodiment the mesh cover having a proximal end 62 and a distal end 60 is attached to the proximal end 64 and distal end 66 of the stent 10 using conventional metal-polymer or polymer-polymer adhesion techniques such as adhesive bonding, shrink bonding, laser melting and the like. In order to secure the mesh cover to the stent, only a small portion of the mesh cover material need to bonded to the stent. Further, The drug-loaded polymeric mesh has a thickness in the range of about 0.005 to about 0.1 mm (0.0002 to 0.004 inches). An adhesive such as medical grade silicone can be used to bond the mesh cover material to the stent.

The stent 10 of the present invention and similar stent structures can be made in many ways. One method of making the stent rings 16 is to cut a tubular member, such as stainless steel tubing to remove portions of the tubing in the desired pattern for the stent, leaving relatively untouched the portions of the metallic tubing which are to form the rings. In accordance with the invention, it is preferred to cut the tubing in the desired pattern using a machine-controlled laser, which process is well known in the art.

After laser cutting, the stent rings are preferably electrochemically polished in an acidic aqueous solution such as a solution of ELECTRO-GLO #300, sold by the ELECTROGLO Co., Inc. in Chicago, Ill., which is a mixture of sulfuric acid, carboxylic acids, phosphates, corrosion inhibitors and a biodegradable surface active agent. The bath temperature is maintained at about 110-135° F. and the current density is about 0.4 to about 1.5 amps per square inch. Cathode to anode area should be at least about two to one. There are numerous other methods to electropolish stents, which are known in the art.

The foregoing laser cutting process to form the cylindrical rings 16 can be used with metals other than stainless steel including cobalt-chromium, titanium, tantalum, platinum, nickel-titanium, and other biocompatible metals suitable for use in humans, and typically used for intravascular stents. Further, while the formation of the cylindrical rings is described in detail, other processes of forming the rings are possible and are known in the art, such as by using chemical etching, electronic discharge machining, stamping, and other processes.

While the invention has been illustrated and described herein, in terms of its use as an intravascular stent, it will be apparent to those skilled in the art that the stent can be used in other body lumens. Further, particular sizes and dimensions, materials used, and the like have been described herein and are provided as examples only. Likewise, the invention is not limited to any particular method of forming the underlying medical device structure. Other modifications and improvements may be made without departing from the scope of the invention. Accordingly, it is not intended that the invention be limited, except as by the appended claims.

What is claimed is:

1. A method for treating a body lumen with a drug-delivery stent assembly, comprising:
providing a pattern of struts interconnected to form a stent structure that contacts the wall of a body lumen to maintain the patency of the lumen;
attaching a stent cover having a delivery sheath fabricated from a mesh to at least a portion of an outside surface area of the stent structure to form the stent assembly;
loading the delivery sheath with at least one therapeutic agent for the release thereof in the body lumen;
intraluminally delivering the stent assembly in the body lumen;

providing a radially outward directed force to the stent cover; and plastically deforming at least a portion of the stent cover in response to the radially outward directed force so that the deformed portions neck down or break thereby providing less resistance to expansion of the stent assembly, wherein the stent cover is attached to the stent structure at a stent structure distal end and a stent structure proximal end so that the stent cover is free to stretch in a mid-cover section as the stent expands.

2. The method of claim 1, wherein the radially outward force is delivered to the stent structure by inflation of an expandable member on a catheter.

3. The method of claim 1, wherein the radially outward directed force is provided by a self-expanding stent structure.

4. The method of claim 1, wherein the therapeutic agent is selected from the group consisting essentially of antiplatelets, anticoagulants, antifibrins, antithrombins, anti-inflammatories and antiproliferatives.

5. The method of claim 1, wherein the mesh stent cover comprises a polymer.

6. The method of claim 5, wherein the polymer is selected from the group consisting of PMMA, EVAL, PBMA, PGA, PEG, HA, PEA, PGS and PLLA.

7. The method of claim 1, wherein the pattern of struts includes a plurality of flexible cylindrical rings being expandable in a radial direction, each of the rings having a first delivery diameter and a second implanted diameter and being aligned on a common longitudinal axis.

8. The method of claim 1, wherein the stent structure is formed of a metallic material.

9. The method of claim 8, wherein the metallic material forming the stent structure is taken from the group consisting essentially of stainless steel, platinum, titanium, tantalum, nickel-titanium, cobalt chromium, and alloys thereof.

10. The method of claim 1, wherein the radially outward directed force is provided by the stent expanding from a first delivery diameter to a second implanted diameter.

11. The method of claim 1, wherein the mesh stent cover is prepared in situ by weaving.

12. The method of claim 1, wherein the mesh stent cover is braided on the stent.

13. The method of claim 1, wherein the stent cover is attached to the stent structure by an adhesive.

14. The method of claim 1, wherein upon expansion of the stent structure, the stent cover plastically deforms so that the stent cover is held by the stent structure against the wall of the body lumen.

15. The method of claim 1, wherein the stent cover includes a polymeric material as a barrier layer to further control delivery of the therapeutic agent at the treatment site.

16. The method of claim 1, wherein the therapeutic agent loading range is about 30 to 60 percent by weight.

17. The method of claim 1, wherein the mesh stent cover is configured to neck down in response to a stent structure expansion of at least 400 percent.

18. The method of claim 1, wherein the mesh includes a plurality of mesh members and one or more positions between the mesh members that will break in response to the radially outward directed force.

19. A method for treating a body lumen with a drug-delivery stent assembly, comprising:

providing a pattern of struts interconnected to form a stent structure that contacts the wall of a body lumen to maintain the patency of the lumen;

attaching a stent cover having a delivery sheath fabricated from a mesh to at least a portion of an outside surface area of the stent structure to form the stent assembly;

loading the delivery sheath with at least one therapeutic agent for the release thereof in the body lumen;

intraluminally delivering the stent assembly in the body lumen;

providing a radially outward directed force to the stent cover; and plastically deforming at least a portion of the stent cover in response to the radially outward directed force so that the deformed portions neck down or break thereby providing less resistance to expansion of the stent assembly, wherein the therapeutic agent loading range is about 30 to 60 percent by weight.

20. The method of claim 19, wherein the mesh includes weakened points at selected locations to provide nonrandom breakage in response to the radially outward directed force.

21. A method for treating a body lumen with a drug-delivery stent assembly, comprising:

providing a pattern of struts interconnected to form a stent structure that contacts the wall of a body lumen to maintain the patency of the lumen;

attaching a stent cover having a delivery sheath fabricated from a mesh to at least a portion of an outside surface area of the stent structure to form the stent assembly;

loading the delivery sheath with at least one therapeutic agent for the release thereof in the body lumen;

intraluminally delivering the stent assembly in the body lumen;

providing a radially outward directed force to the stent cover; and plastically deforming at least a portion of the stent cover in response to the radially outward directed force so that the deformed portions neck down or break thereby providing less resistance to expansion of the stent assembly, wherein the mesh stent cover is configured to neck down in response to a stent structure expansion of at least 400 percent.

22. The method of claim 21, wherein the mesh includes mesh members, at least one of the mesh members including a breakable point that breaks in response to the radially outward directed force to allow the unbroken mesh members to deploy against the body lumen.

23. A method for treating a body lumen with a drug-delivery stent assembly, comprising:

providing a pattern of struts interconnected to form a stent structure that contacts the wall of a body lumen to maintain the patency of the lumen;

attaching a stent cover having a delivery sheath fabricated from a mesh to at least a portion of an outside surface area of the stent structure to form the stent assembly;

loading the delivery sheath with at least one therapeutic agent for the release thereof in the body lumen;

intraluminally delivering the stent assembly in the body lumen;

providing a radially outward directed force to the stent cover; and plastically deforming at least a portion of the stent cover in response to the radially outward directed force so that the deformed portions neck down or break thereby providing less resistance to expansion of the stent assembly, wherein the stent cover is attached to the stent structure by laser bonding.

24. A method for treating a body lumen with a drug-delivery stent assembly, comprising:

providing a pattern of struts interconnected to form a stent structure that contacts the wall of a body lumen to maintain the patency of the lumen;

attaching a stent cover having a delivery sheath fabricated from a mesh to at least a portion of an outside surface area of the stent structure to form the stent assembly;

loading the delivery sheath with at least one therapeutic agent for the release thereof in the body lumen;

intraluminally delivering the stent assembly in the body lumen;

providing a radially outward directed force to the stent cover; and plastically deforming at least a portion of the stent cover in response to the radially outward directed force so that the deformed portions neck down or break thereby providing less resistance to expansion of the stent assembly, wherein the stent cover is made using at least one polymeric process consisting of injection molding, laser cutting, and slip casting.

* * * * *